United States Patent [19]

Yamamoto et al.

[11] 4,179,560
[45] Dec. 18, 1979

[54] IMIDAZO- AND PYRIMIDO[2,1-b]QUINAZOLINES AND PREPARATION THEREOF

[75] Inventors: Michihiro Yamamoto; Shigeaki Morooka; Masao Koshiba, all of Nishinomiya; Shigeho Inaba, Takarazuka; Hisao Yamamoto, Kobe, all of Japan

[73] Assignee: Sumitomo Chemical Company, Limited, Osaka, Japan

[21] Appl. No.: 553,676

[22] Filed: Feb. 27, 1975

[30] Foreign Application Priority Data

Feb. 28, 1974 [JP] Japan .................. 49-24500

[51] Int. Cl.² .................. A61K 31/395; C07D 487/04
[52] U.S. Cl. .................. 544/250; 544/247; 544/248; 544/251; 544/286; 424/250
[58] Field of Search .................. 260/256.4 F

[56] References Cited

U.S. PATENT DOCUMENTS 3,621,025  11/1971  Jen et al. .................. 260/256.4 F
3,887,559   6/1975  Hardtmann .................. 260/256.4 F Primary Examiner—Donald G. Daus
Assistant Examiner—James H. Turnipseed
Attorney, Agent, or Firm—Stevens, Davis, Miller & Mosher

[57] ABSTRACT

Imidazo- and pyrimido[2,1-b]quinazolines of the formula,

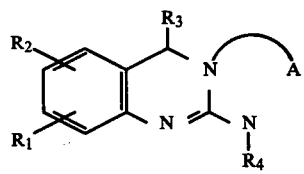

wherein $R_1$ and $R_2$ are independently hydrogen, halogen, trifluoromethyl, nitro, $C_{1-4}$ alkyl or $C_{1-4}$ alkoxy, or $R_1$ and $R_2$ may together represent methylenedioxy; $R_3$ is hydrogen, $C_{1-4}$ alkyl, phenyl or substituted phenyl of the formula,

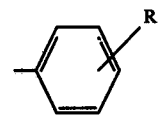

(wherein R is halogen, $C_{1-4}$ alkyl or $C_{1-4}$ alkoxy); $R_4$ is hydrogen, $C_{1-4}$ alkyl or aralkyl; and A is $C_{2-3}$ alkylene wich may be optionally substituted by one or two $C_{1-2}$ alkyl radicals, and pharmaceutically acceptable acid addition salts thereof, are prepared by reacting a compound of the formula,

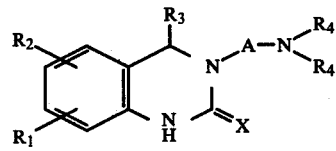

wherein $R_1$, $R_2$, $R_3$, $R_4$ and A are as defined above; and X is oxygen or sulfur, with a halogenating agent at a temperature of about 30° C. to about 180° C. In the above imidaxo- and pyrimido[2,1-b]quinazolines, those having $C_{1-4}$ alkyl, or

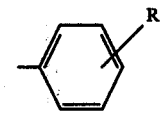

as $R_3$ are novel compounds and show antidepressant and/or antihypertensive activities.

4 Claims, No Drawings

IMIDAZO- AND PYRIMIDO[2,1-b]QUINAZOLINES AND PREPARATION THEREOF

This invention relates to novel imidazo-quinazolines and pyrimidoquinazolines as well as to a novel process for preparing the same.

More particularly, the present invention pertains to imidazo[2,1-b]quinazolines and pyrimido-[2,1-b]quinazolines having pharmacological activity.

The compounds of the present invention are represented by the formula,

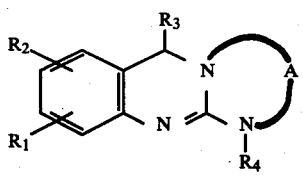

wherein $R_1$ and $R_2$ are independently hydrogen, halogen, trifluoromethyl, nitro, $C_{1-4}$ alkyl or $C_{1-4}$ alkoxy, or $R_1$ and $R_2$ may together represent methylenedioxy; $R_3$ is hydrogen, $C_{1-4}$ alkyl, phenyl or substituted phenyl of the formula

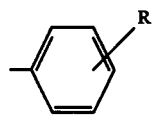

(wherein R is halogen, $C_{1-4}$ alkyl or $C_{1-4}$ alkoxy); $R_4$ is hydrogen, $C_{1-4}$ alkyl or aralkyl; and A is $C_{2-3}$ alkylene which may be optionally substituted by one or two $C_{1-2}$ alkyl radicals; or pharmaceutically acceptable acid addition salts thereof.

In the compounds of the above formula [I] and elsewhere in the specification, the term "halogen" may be fluorine, chlorine, bromine or iodine; the term "alkyl" includes both straight or branched chain saturated aliphatic hydrocarbon radicals, and the term "$C_{1-4}$ alkyl" may be methyl, ethyl, n-propyl, isopropyl, n-butyl or isobutyl; the term "$C_{1-4}$ alkoxy" may be methoxy, ethoxy, n-propoxy, isopropoxy, n-butoxy or isobutoxy; the term "aralkyl" may, for example, be benzyl, phenethyl or halobenzyl; and the term "$C_{2-3}$ alkylene" in the symbol A, which may optionally have one or two $C_{1-2}$ alkyl radicals, includes, for example, ethylene, 1-methylethylene, 2-methylethylene, 1,1-dimethylethylene, 1-ethylethylene or trimethylene.

Some of the compounds of the formula [I] have been known and described in Belgian Pat. No. 760,013. But the compounds of the formula,

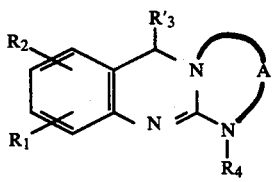

wherein $R_1$, $R_2$, $R_4$ and A are as defined above; and $R'_3$ is $C_{1-4}$ alkyl, phenyl or substituted phenyl of the formula

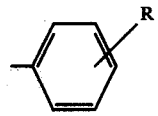

(wherein R is halogen, $C_{1-4}$ alkyl or $C_{1-4}$ alkoxy), are novel and they are found to have very interesting pharmacological activities, for example, antidepressant and/or antihypertensive activities, which render them useful as synthetic medicinals. Illustratively, 1-ethyl-5-phenyl-7-chloro-1,2,3,5-tetrahydroimidazo-[2,1-b]quinazoline shows as potent antidepressant activity as that of imipramine against reserpine at oral dosage of 25 mg/kg in the animal test.

Thus, the present invention provides a pharmaceutical composition containing as an active ingredient one or more compounds of the formula [I-a] in admixture with a pharmaceutically acceptable diluent or carrier.

Accordingly, an object of the present invention is to provide a novel and useful process for producing the compounds of the formula [I]. Another object of the present invention is to provide novel compounds of the formula [I-a] possessing excellent pharmacological properties, particularly as antidepressants.

According to the process of the present invention, the imidazoquinazolines and pyrimidoquinazolines of the formula [I] may be smoothly prepared by reacting a quinazoline derivative of the formula,

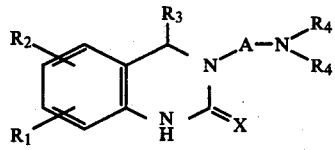

wherein $R_1$, $R_2$, $R_3$, $R_4$ and A are as defined above; and X is oxygen or sulfur, with a halogenating agent such as a phosphorus oxyhalide, a phosphorus trihalide, a phosphorus pentahalide, thionyl chloride or a mixture thereof.

Such a process for converting a 3-(ω-amino-alkyl)-3,4-dihydro-2-(1H)-quinazolinone derivative into an imidazo- or pyrimido[2,1-b]quinazoline derivative has, as far as we known, not been described or suggested in any of the literature. Moreover, this process is very convenient and much improved over the known processes.

The reaction according to the present invention is effected by heating a mixture of the reactants at a temperature from about 30° C. to about 180° C. for a period of preferably from about one to ten hours. If desired, the reaction may be carried out in the presence of a suitable inert organic solvent. However, the use of a solvent is not essential since an excess of the halogenating agent can be used for this purpose.

Suitable inert solvents are, for example, benzene, toluene, xylene, chlorobenzene, nitrobenzene, chloroform, 1,2-dichloroethane, 1,1,1-trichloroethane, tetrahydrofuran, dioxane or dimethylformamide.

The halogenating agent employed in the reaction is preferably selected from the group consisting of phosphorus oxychloride, phosphorus oxybromide, phosphorus trichloride, phosphorus tribromide, phosphorus pentachloride, phosphorus pentabromide, thionyl chloride and a mixture thereof.

A tertiary organic base such as triethylamine, N,N-dimethylaniline or pyridine may be used to advantage the process of the present invention.

The quinazoline derivatives of the formula [II] are known and can be readily prepared as described in British Pat. No. 1,344,658, for example, by the reaction of an appropriate 2-trihalogenoacetamidophenyl ketone derivative with an alkylene diamine derivative, followed by reduction with sodium borohydride and the like. Such quinazolines can also be prepared by the reaction of a compound of the formula,

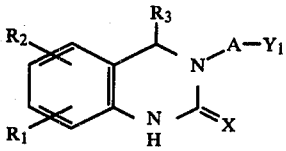  [III]

wherein $R_1$, $R_2$, $R_3$, A and X are as defined above; and $Y_1$ is halogen or arylsulfonyl (e.g. benzenesulfonyl, p-toluenesulfonyl), with a compound of the formula,

  [IV]

wherein $R_4$ is as defined above, by known procedures.

Alternatively, the afore-mentioned novel compounds of the formula [I-a] may be prepared by reacting a compound of the formula,

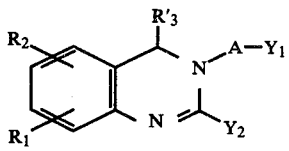  [V]

wherein $R_1$, $R_2$, $R'_3$, A and $Y_1$ are as defined above; and $Y_2$ is halogen or $C_{1-4}$ alkylthio, with a compound of the formula,

  [VI]

wherein $R_4$ is as defined above.

The reaction may be carried out optionally in the presence of an inert solvent at a temperature in the range of from room temperature to about 160° C. The solvents preferably employed are, for example, methanol, ethanol, propanol, butanol, methoxyethanol, tetrahydrofuran, dioxane, water, chloroform, pyridine, dimethylformamide or dimethylsulfoxide. When an excess of the reactant of the formula [VI] is employed, the reaction may be carried out in the absence of the solvent at elevated temperatures, if desired, in a sealed reactor.

The compounds of the formula [IV] employed as a starting material can be prepared, for example, from an available compound of the formula,

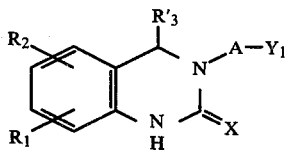  [III-a]

wherein $R_1$, $R_2$, $R'_3$, A, X and $Y_1$ are as defined above, by established procedures.

The imidazoquinazolines and pyrimidoquinazolines of the present invention may form acid addition salts thereof and those pharmaceutically acceptable salts are also included within the scope of the present invention. The acid addition salts may be produced from the corresponding free bases by conventional procedures. Such salts include, for example, the hydrochloride, hydrobromide, sulfate, phosphate, acetate, succinate, fumarate, citrate and tartrate.

According to the processes of the present invention, there are obtained, for example, the following imidazoquinazolines and pyrimidoquinazolines.

1,2,3,5-Tetrahydroimidazo[2,1-b]quinazoline
7-Chloro-1,2,3,5-tetrahydroimidazo[2,1-b]-quinazoline
8-Chloro-1,2,3,5-tetrahydroimidazo[2,1-b]-quinazoline
7-Nitro-1,2,3,5-tetrahydroimidazo[2,1-b]-quinazoline
7,8-Methylenedioxy-1,2,3,5-tetrahydroimidazo[2,1-b]quinazoline
5-Methyl-1,2,3,5-tetrahydroimidazo[2,1-b]quinazoline
5-Methyl-7-chloro-1,2,3,5-tetrahydroimidazo[2,1-b]quinazoline
5-Phenyl-1,2,3,5-tetrahydroimidazo[2,1-b]quinazoline
5-Phenyl-7-chloro-1,2,3,5-tetrahydroimidazo[2,1-b]quinazoline
5-Phenyl-7-bromo-1,2,3,5-tetrahydroimidazo[2,1-b]quinazoline
5-Phenyl-7-nitro-1,2,3,5-tetrahydroimidazo[2,1-b]quinazoline
2-Methyl-1,2,3,5-tetrahydroimidazo[2,1-b]quinazoline
1-Ethyl-1,2,3,5-tetrahydroimidazo[2,1-b]quinazoline
1,5-Dimethyl-1,2,3,5-tetrahydroimidazo[2,1-b]quinazoline
1-Ethyl-5-methyl-7-chloro-1,2,3,5-tetrahydroimidazo[2,1-b]quinazoline
1-Methyl-5-phenyl-7-chloro-1,2,3,5-tetrahydroimidazo[2,1-b]quinazoline
1-Methyl-5-phenyl-7-nitro-1,2,3,5-tetrahydroimidazo[2,1-b]quinazoline
1-Ethyl-5-phenyl-7-trifluoromethyl-1,2,3,5-tetrahydroimidazo[2,1-b]quinazoline
1-Ethyl-5phenyl-7-methoxy-1,2,3,5-tetrahydroimidazo[2,1-b]quinazoline
1-Ethyl-5-phenyl-7,8-methylenedioxy-1,2,3,5-tetrahydroimidazo[2,1-b]quinazoline
1-Ethyl-5-phenyl-7-nitro-1,2,3,5-tetrahydroimidazo[2,1-b]quinazoline
1-Ethyl-5-phenyl-7-chloro-1,2,3,5-tetrahydroimidazo[2,1-b]quinazoline
1-Ethyl-5-phenyl-7-methyl-1,2,3,5-tetrahydroimidazo[2,1-b]quinazoline
1-Ethyl-5-phenyl-1,2,3,5-tetrahydroimidazo[2,1-b]quinazoline
1-Ethyl-5-phenyl-7,9-dichloro-1,2,3,5-tetrahydroimidazo[2,1-b]quinazoline
1-(n-Propyl)-5-phenyl-7-chloro-1,2,3,5-tetrahydroimidazo[2,1-b]quinazoline
1-(Isopropyl)-5-phenyl-7-chloro-1,2,3,5-tetrahydroimidazo[2,1-b]quinazoline
1-Benzyl-5-phenyl-7-chloro-1,2,3,5-tetrahydroimidazo[2,1-b]quinazoline
1-Ethyl-5-(o-fluorophenyl)-7-chloro-1,2,3,5-tetrahydroimidazo[2,1-b]quinazoline
1-Ethyl-5-(p-tolyl)-1,2,3,5-tetrahydroimidazo[2,1-b]quinazoline
6-Methyl-1,2,3,4-tetrahydro-6H-pyrimido[2,1-b]quinazoline
6-Phenyl-1,2,3,4-tetrahydro-6H-pyrimido[2,1-b]-quinazoline 6-Phenyl-8-chloro-1,2,3,4-tetrahydro-6H-pyrimido[2,1-b]quinazoline 1-Methyl-6-phenyl-8-chloro-1,2,3,4-tetrahydro-6H-pyrimido[2,1-b]quinazoline 1-Ethyl-6-methyl-1,2,3,4,-tetrahydro-6H-pyrimido[2,1-b]quinazoline 1-Ethyl-6-phenyl-1,2,3,4-tetrahydro-6H-pyrimido[2,1-b]quinazoline 1-Ethyl-6-phenyl-8-chloro-1,2,3,4-tetrahydro-6H-pyrimido[2,1-b]quinazoline 1-Ethyl-6-phenyl-8-nitro-1,2,3,4-tetrahydro-6H-pyrimido[2,1-b]quinazoline 1-(n-Propyl)-6-phenyl-8-chloro-1,2,3,4-tetrahydro-6H-pyrimido[2,1-b]quinazoline 1-(Isopropyl)-6-phenyl-8-chloro-1,2,3,4-tetrahydro-6H-pyrimido[2,1-b]quinazoline This invention is further disclosed in the following Examples of more preferred embodiments thereof, which are presented for the purpose of illustration and it is not intended to limit the scope of the invention.

EXAMPLE 1

A mixture of 2.15 g of 3-(2-dimethylaminoethyl)-4-phenyl-6-chloro-3,4-dihydro-2(1H)-quinazolinone and 10 ml of phosphorus oxychloride was refluxed with stirring for 2 hours. The resulting solution was evaporated in vacuo to dryness and the resulting residue was dissolved in chloroform. The solution was washed with cold water and then with dilute ammonia water, and dried over anhydrous sodium sulfate. The solvent was then removed under reduced pressure to give 1.85 g of 1-ethyl-5-phenyl-7-chloro-1,2,3,5-tetrahydroimidazo[2,1-b]quinazoline. Recrystallization from ethanol gave colorless prisms, m.p. 145°–146° C.

EXAMPLE 2

The following compounds were obtained by the manner similar to that described in Example 1.

1,2,3,5-Tetrahydroimidazo[2,1-b]quinazoline hydrochloride, m.p. 251° C.;

1-Methyl-5-phenyl-7-chloro-1,2,3,5-tetrahydroimidazo[2,1-b]quinazoline, m.p. 182°–184° C.;

1-(n-Propyl)-5-phenyl-7-chloro-1,2,3,5-tetrahydroimidazo[2,1-b]quinazoline, m.p. 144°–145° C.;

1-Benzyl-5-phenyl-7-chloro-1,2,3,5-tetrahydroimidazo[2,1-b]quinazoline hydrochloride, m.p. 174°–175° C.;

1-Methyl-6-phenyl-8-chloro-1,2,3,5-tetrahydro-6H-pyrimido[2,1-b]quinazoline, m.p. 169°–171° C.

EXAMPLE 3

A mixture of 3.21 g of 3-(2-chloroethyl)-4-phenyl-6-chloro-3,4-dihydro-2(1H)-quinazolinone and 10 g of phosphorus oxychloride was heated with stirring at 105° C. for 20 hours. The resulting solution was evaporated in vacuo to dryness and the resulting residue was dissolved in chloroform. The chloroform solution was washed with an aqueous sodium bicarbonate solution and then with water, and dried over anhydrous sodium sulfate. The solvent was removed under reduced pressure to give 2,6-dichloro-3-(2-chloroethyl)-4-phenyl-3,4-dihydroquinazoline. The crude solid was chromatographed on silica gel using chloroform as an eluting solvent. Removal of the solvent and recrystallization of the residue from a mixture of benzene and petroleum benzin gave 0.60 g of pure product, m.p. 169°–170° C. To a solution of 0.34 g of 2,6-dichloro-3-(2-chloroethyl)-4-phenyl-3,4-dihydroquinazoline in 2 ml of dimethylformamide was added 0.59 g of n-propylamine and the mixture was heated at 105° C. for 5 hours. After cooling, 10 ml of water was added to the reaction mixture and the resulting mixture was extracted with chloroform. The organic phase was separated, washed with water and dried over anhydrous sodium sulfate. The solvent was removed under reduced pressure and the residue was chromatographed on silica gel using chloroform as an eluting solvent to give 0.24 g of 1-(n-propyl)-5-phenyl-7-chloro-1,2,3,5-tetrahydroimidazo[2,1-b]quinazoline hydrochloride. Recrystallization from a mixture of ethanol and diisopropyl ether gave slightly brown fine crystals, m.p. 258° C.

What is claimed is:

1. A process for preparing a compound of the formula,

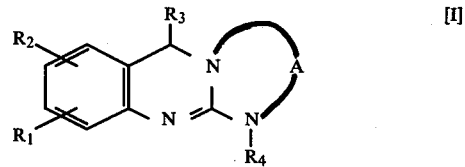

wherein $R_1$ and $R_2$ are independently hydrogen, halogen, trifluoromethyl, nitro, $C_{1-4}$ alkyl or $C_{1-4}$ alkoxy, or $R_1$ and $R_2$ may together represent methylenedioxy; $R_3$ is hydrogen, $C_{1-4}$ alkyl, phenyl or substituted phenyl of the formula

(wherein R is halogen, $C_{1-4}$ alkyl or $C_{1-4}$ alkoxy); $R_4$ is hydrogen, $C_{1-4}$ alkyl or benzyl; and A is $C_{2-3}$ alkene which may be optionally substituted by one or two $C_{1-2}$ alkyl radicals; or a pharmaceutically acceptable acid addition salt thereof, which comprises the step of reacting a compound of the formula,

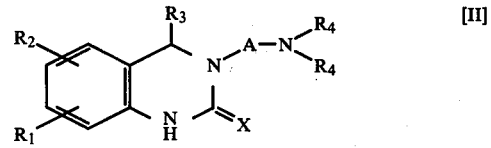

wherein $R_1$, $R_2$, $R_3$, $R_4$ and A are as defined above; and X is oxygen or sulfur, with a halogenating agent selected from the group consisting of phosphorus oxyhalide, phosphorus trihalide, phosphorus pentahalide, thionyl chloride and a mixture thereof, at a temperature within the range of from about 30° C. to about 180° C.

2. A process according to claim 1, wherein the halogenating agent is selected from the group consisting of phosphorus oxychloride, phosphorus oxybromide, phosphorus trichloride, phosphorus tribromide, phosphorus petachloride, phosphorus pentabromide, thionyl chloride and a mixture thereof.

3. A process according to claim 1, wherein the halogenating agent is selected from the group consisting of phosphorus oxychloride and phosphorus oxybromide.

4. A process according to claim 1, wherein in the compound of the formula [I] $R_1$ and $R_2$ are independently hydrogen or halogen; $R_3$ is hydrogen or phenyl; $R_4$ is as defined in claim 1; and A is $C_{2-3}$ alkylene.

* * * * *